(12) United States Patent
Leuck et al.

(10) Patent No.: US 11,129,661 B2
(45) Date of Patent: Sep. 28, 2021

(54) COMBINATION ULTRASONIC AND ELECTROSURGICAL SYSTEM HAVING EEPROM AND ASIC COMPONENTS

(71) Applicant: ETHICON LLC, Guaynabo, PR (US)

(72) Inventors: Stephen M. Leuck, Milford, OH (US); Eitan T. Wiener, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 585 days.

(21) Appl. No.: 15/967,764

(22) Filed: May 1, 2018

(65) Prior Publication Data

US 2018/0333186 A1     Nov. 22, 2018

Related U.S. Application Data

(60) Provisional application No. 62/509,351, filed on May 22, 2017.

(51) Int. Cl.
*A61B 18/00* (2006.01)
*A61B 90/00* (2016.01)
(Continued)

(52) U.S. Cl.
CPC ...... *A61B 18/00* (2013.01); *A61B 17/320092* (2013.01); *A61B 18/1206* (2013.01);
(Continued)

(58) Field of Classification Search
CPC .... A61B 17/320068; A61B 17/320092; A61B 18/00; A61B 18/12; A61B 18/1206;
(Continued)

(56) References Cited

U.S. PATENT DOCUMENTS 5,322,055 A   6/1994  Davison et al.
5,400,267 A   3/1995  Denen et al.
(Continued)

FOREIGN PATENT DOCUMENTS

DE   10 2014 116065 A1   5/2016
EP      2 371 314 A2    10/2011
(Continued)

OTHER PUBLICATIONS

U.S. Appl. No. 15/967,746.
(Continued)

*Primary Examiner* — Michael F Peffley
*Assistant Examiner* — Khadijeh A Vahdat
(74) *Attorney, Agent, or Firm* — Frost Brown Todd LLC

(57) ABSTRACT

A surgical system includes a surgical instrument having a body, an ultrasonic transducer, a shaft extending distally from the body, and an end effector at a distal end of the shaft and being operable to treat tissue with ultrasonic energy. An accessory device is configured to operatively couple the surgical instrument with a generator operable to power the surgical instrument to provide ultrasonic energy. A primary EEPROM is provided within the instrument body and is operable to track usage of the surgical instrument. The system further includes at least one of: an accessory EEPROM integrated into the accessory device and being operable to track usage of the accessory device; a transducer EEPROM integrated into the ultrasonic transducer and being operable to track usage of the ultrasonic transducer; or an ASIC integrated into the accessory device and being operable to communicate with the generator regarding a state of the surgical instrument.

20 Claims, 11 Drawing Sheets

(51) Int. Cl.
*A61B 18/12* (2006.01)
*A61B 18/14* (2006.01)
*A61B 17/32* (2006.01)
*A61B 17/00* (2006.01)
*A61B 17/29* (2006.01)

(52) U.S. Cl.
CPC ............... *A61B 18/1445* (2013.01); *A61B 2017/00017* (2013.01); *A61B 2017/00137* (2013.01); *A61B 2017/2929* (2013.01); *A61B 2017/2932* (2013.01); *A61B 2017/320072* (2013.01); *A61B 2017/320074* (2017.08); *A61B 2017/320075* (2017.08); *A61B 2017/320078* (2017.08); *A61B 2017/320088* (2013.01); *A61B 2017/320094* (2017.08); *A61B 2017/320095* (2017.08); *A61B 2018/0063* (2013.01); *A61B 2018/00077* (2013.01); *A61B 2018/00083* (2013.01); *A61B 2018/00607* (2013.01); *A61B 2018/00988* (2013.01); *A61B 2018/00994* (2013.01); *A61B 2018/126* (2013.01); *A61B 2018/1452* (2013.01); *A61B 2018/1457* (2013.01); *A61B 2090/0803* (2016.02)

(58) Field of Classification Search
CPC ............... A61B 18/14; A61B 18/1445; A61B 18/1448; A61B 2017/00017; A61B 2017/00137; A61B 2017/00738; A61B 2017/00929; A61B 2017/2929; A61B 2017/2932; A61B 2017/320072; A61B 2017/320074; A61B 2017/003275; A61B 2017/320078; A61B 2017/320088; A61B 2017/320094; A61B 2017/320095; A61B 2018/00077; A61B 2018/00083; A61B 2018/00136; A61B 2018/00178; A61B 2018/00577; A61B 2018/00607; A61B 2018/0063; A61B 2018/00988; A61B 2018/00994; A61B 2018/126; A61B 2018/142; A61B 2018/1452; A61B 2018/1457; A61B 2090/0803
USPC .......................... 606/51–52, 169, 205–207
See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,873,873 A | 2/1999 | Smith et al. | |
| 5,878,193 A | 3/1999 | Wang et al. | |
| 5,944,737 A | 8/1999 | Tsonton et al. | |
| 5,980,510 A | 11/1999 | Tsonton et al. | |
| 6,231,565 B1 | 5/2001 | Tovey et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,500,176 B1 | 12/2002 | Truckai et al. | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,025,630 B2 | 9/2011 | Murakami et al. | |
| 8,057,498 B2 | 11/2011 | Robertson | |
| 8,058,771 B2 | 11/2011 | Giordano et al. | |
| 8,147,488 B2 | 4/2012 | Masuda | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,939,974 B2 | 1/2015 | Boudreaux et al. | |
| 8,986,302 B2 | 3/2015 | Aldridge et al. | |
| 9,017,326 B2 | 4/2015 | DiNardo et al. | |
| 9,039,690 B2 | 5/2015 | Kersten et al. | |
| 9,089,327 B2 | 7/2015 | Worrell et al. | |
| 9,095,367 B2 | 8/2015 | Olson et al. | |
| 9,101,385 B2 | 8/2015 | Shelton, IV et al. | |
| 9,107,690 B2 | 8/2015 | Bales, Jr. et al. | |
| 9,161,803 B2 | 10/2015 | Yates et al. | |
| 9,301,759 B2 | 4/2016 | Spivey et al. | |
| 9,402,682 B2 | 8/2016 | Worrell et al. | |
| 9,545,253 B2 | 1/2017 | Worrell et al. | |
| 9,572,622 B2 | 2/2017 | Shelton, IV et al. | |
| 9,681,912 B2 | 6/2017 | Tsubuku et al. | |
| 9,724,120 B2 | 8/2017 | Faller et al. | |
| 9,795,436 B2 | 10/2017 | Yates et al. | |
| 9,901,754 B2 | 2/2018 | Yamada | |
| 9,962,222 B2 | 5/2018 | Brustad et al. | |
| 10,010,340 B2 | 7/2018 | Hibner et al. | |
| 10,028,765 B2 | 7/2018 | Hibner et al. | |
| 10,039,595 B2 | 8/2018 | Sakaguchi et al. | |
| 10,201,364 B2 | 2/2019 | Leimbach et al. | |
| 2007/0016236 A1 | 1/2007 | Beaupre | |
| 2012/0078243 A1 | 3/2012 | Worrell et al. | |
| 2013/0282003 A1* | 10/2013 | Messerly ........... A61B 18/1206 606/37 |
| 2014/0135804 A1 | 5/2014 | Weisenburgh, II et al. | |
| 2014/0163541 A1 | 6/2014 | Shelton, IV et al. | |
| 2014/0239037 A1 | 8/2014 | Boudreaux et al. | |
| 2015/0088178 A1 | 3/2015 | Stulen et al. | |
| 2015/0141981 A1 | 5/2015 | Price et al. | |
| 2015/0164538 A1 | 6/2015 | Aldridge et al. | |
| 2015/0358426 A1 | 12/2015 | Kimball et al. | |
| 2015/0374360 A1 | 12/2015 | Scheib et al. | |
| 2016/0022305 A1 | 1/2016 | Lamping et al. | |
| 2016/0302820 A1 | 10/2016 | Hibner et al. | |
| 2016/0324537 A1 | 11/2016 | Green et al. | |
| 2016/0367281 A1 | 12/2016 | Gee et al. | |
| 2017/0000515 A1 | 1/2017 | Akagane | |
| 2017/0000516 A1 | 1/2017 | Stulen et al. | |
| 2017/0000541 A1 | 1/2017 | Yates et al. | |
| 2017/0086876 A1 | 3/2017 | Wiener et al. | |
| 2017/0086908 A1 | 3/2017 | Wiener et al. | |
| 2017/0086909 A1 | 3/2017 | Yates et al. | |
| 2017/0086910 A1 | 3/2017 | Wiener et al. | |
| 2017/0086911 A1 | 3/2017 | Wiener et al. | |
| 2018/0333182 A1 | 11/2018 | Clauda | |

FOREIGN PATENT DOCUMENTS

| | | |
|---|---|---|
| EP | 2 478 861 A2 | 7/2012 |
| EP | 2 641 552 A2 | 9/2013 |
| EP | 3 031 417 A1 | 6/2016 |
| EP | 3 117 790 A1 | 1/2017 |
| EP | 3 287 085 A1 | 2/2018 |
| WO | WO 2016/091400 A1 | 6/2016 |
| WO | WO 2017/027853 A1 | 2/2017 |

(56) References Cited

FOREIGN PATENT DOCUMENTS

| WO | WO 2017/058617 A2 | 4/2017 |
|----|-------------------|--------|
| WO | WO 2017/091377 A1 | 6/2017 |
| WO | WO 2017/100427 A2 | 6/2017 |

OTHER PUBLICATIONS

U.S. Appl. No. 15/967,747.
U.S. Appl. No. 15/967,763.
U.S. Appl. No. 15/967,740, entitled "Combination Ultrasonic and Electrosurgical Instrument Having Electrical Circuits with Shared Return Path," filed May 1, 2018.
U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with Adjustable Energy Modalities and Method for Sealing Tissue and Inhibiting Tissue Resection," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperatue," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.
International Search Report and Written Opinion dated Aug. 22, 2018 for Application No. PCT/US2018/033599, 14 pgs.
International Search Report and Written Opinion dated Jan. 2, 2019 for Application No. PCT/US2018/033603, 23 pgs.
International Search Report and Written Opinion dated Nov. 6, 2018 for Application No. PCT/US2018/033605, 14 pgs.
International Search Report and Written Opinion dated Jan. 2, 2019 for Application No. PCT/US2018/033607, 22 pgs.
International Search Report and Written Opinion dated Nov. 6, 2018 for Application No. PCT/US2018/033608, 14 pgs.
International Search Report and Written Opinion dated Sep. 3, 2018 for Application No. PCT/US2018/033615, 13 pgs.
International Search Report and Written Opinion dated Aug. 22, 2018 for Application No. PCT/US2018/033618, 12 pgs.
International Search Report and Written Opinion dated Oct. 19, 2018 for Application No. PCT/US2018/033619, 20 pgs.
U.S. Appl. No. 62/509,351, entitled "Ultrasonic Instrument With Electrosurgical Features," filed May 22, 2017.
U.S. Appl. No. 15/967,740.
U.S. Appl. No. 15/967,751.
U.S. Appl. No. 15/967,753.
U.S. Appl. No. 15/967,759.
U.S. Appl. No. 15/967,761.
U.S. Pat. No. 10,945,778.
U.S. Pat. No. 10,945,779.

\* cited by examiner

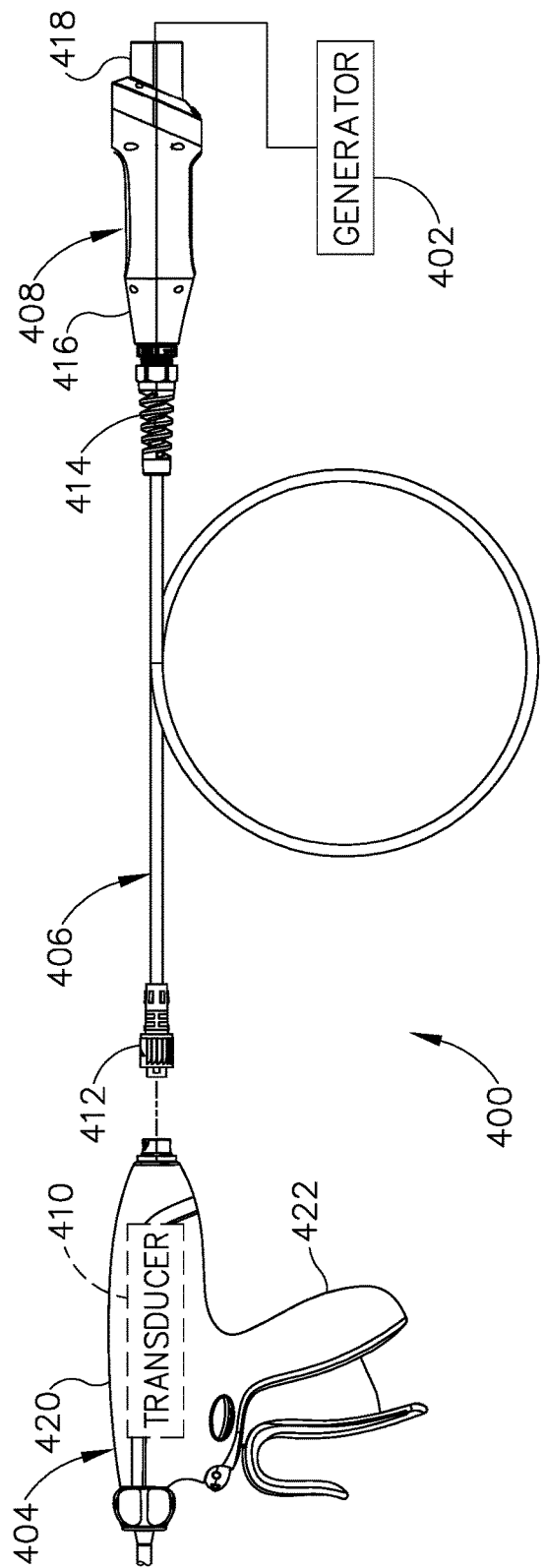
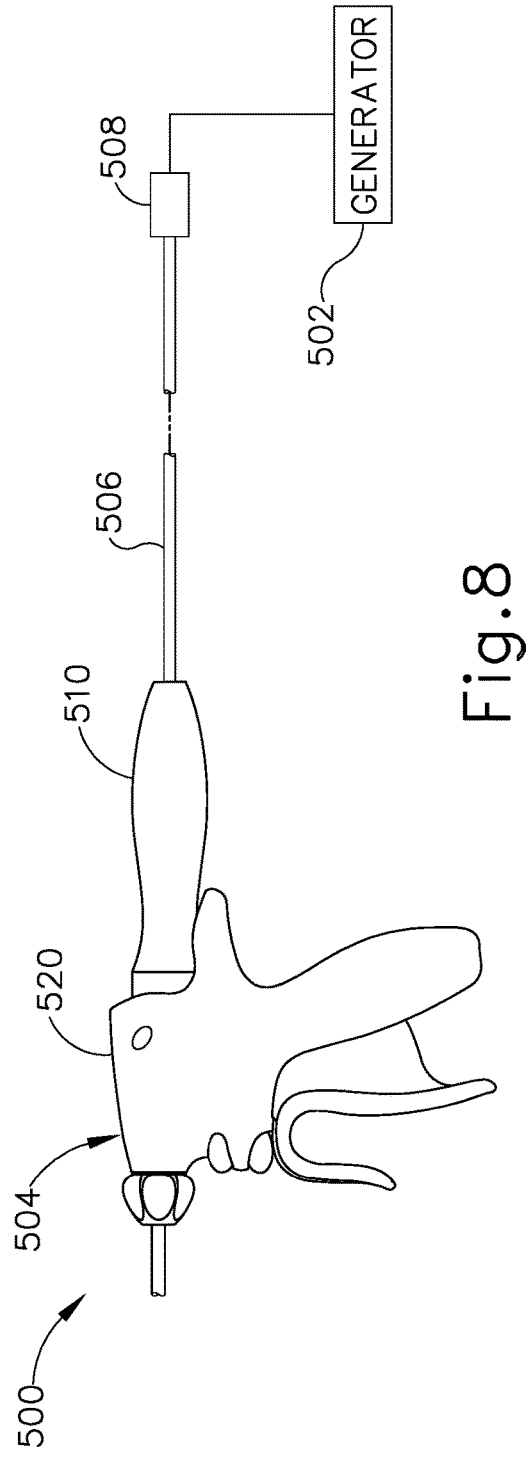

COMBINATION ULTRASONIC AND ELECTROSURGICAL SYSTEM HAVING EEPROM AND ASIC COMPONENTS

This application claims the benefit of U.S. Provisional App. No. 62/509,351, entitled "Ultrasonic Instrument With Electrosurgical Features," filed May 22, 2017, the disclosure of which is incorporated by reference herein.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit lower frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

While various types of ultrasonic surgical instruments and electrosurgical instruments, including combination ultrasonic-electrosurgical instruments, have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7 depicts a partially schematic view of an exemplary surgical system incorporating the surgical instrument of FIG. 1 having an internally mounted ultrasonic transducer, an exemplary power cable, an adapter, and a generator;

FIG. 8 depicts a partially schematic view of another exemplary surgical system incorporating a surgical instrument having an externally mounted ultrasonic transducer, a power cable, an adapter, and a generator;

Figure 1:
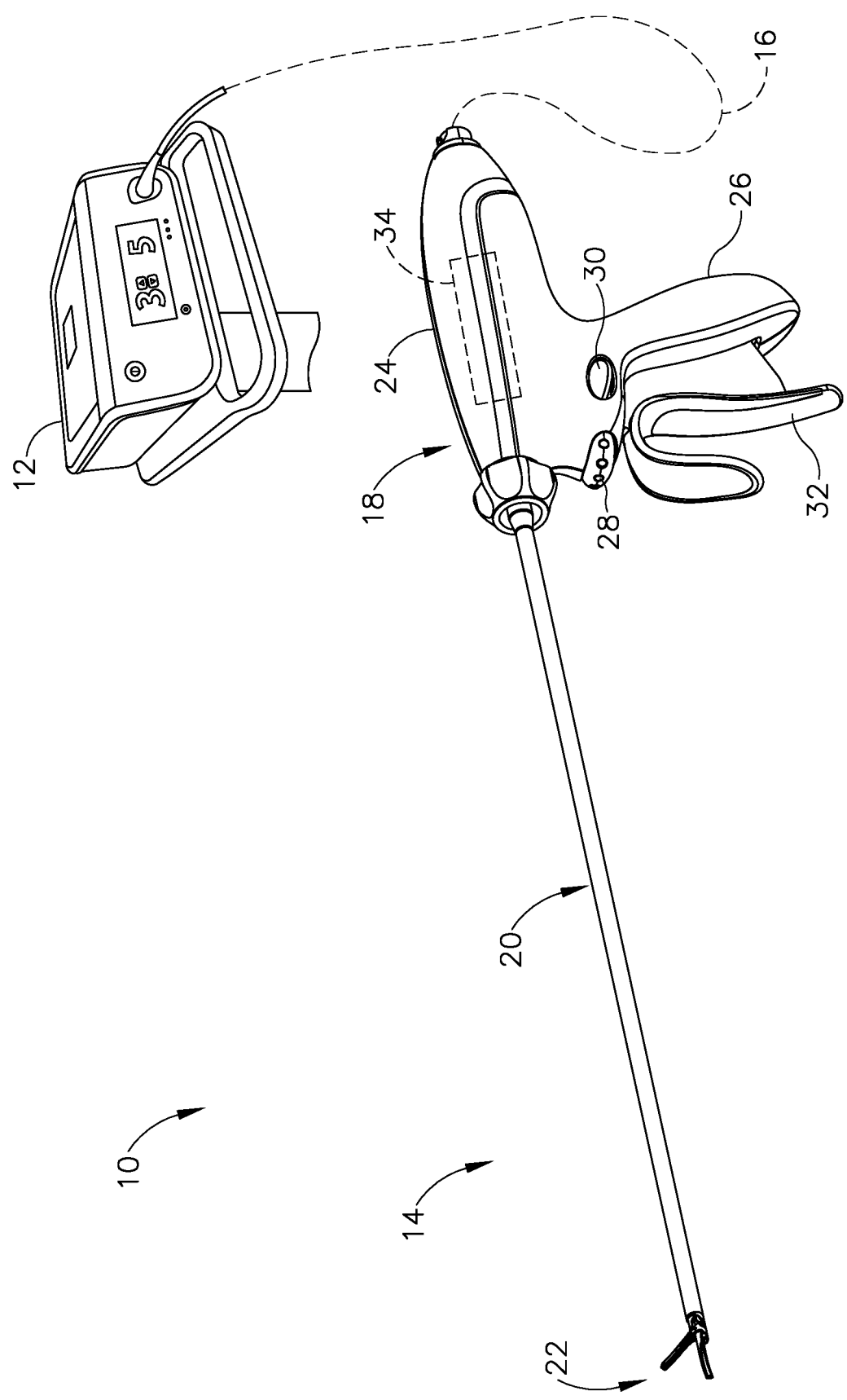
FIG. 1 depicts a perspective view of an exemplary surgical system having a generator and a surgical instrument operable to treat tissue with ultrasonic energy and bipolar RF energy.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical System Having Surgical Instrument with Ultrasonic and Electrosurgical Features FIG. 1 depicts an exemplary surgical system (10) including a generator (12) and a surgical instrument (14). Surgical instrument (14) is operatively coupled with the generator (12) via power cable (16). As described in greater detail below, generator (12) is operable to power surgical instrument (14) to deliver ultrasonic energy for cutting tissue, and electrosurgical bipolar RF energy (i.e., therapeutic levels of RF energy) for sealing tissue. In exemplary configurations, generator (12) is configured to power surgical instrument (14) to deliver ultrasonic energy and electrosurgical bipolar RF energy simultaneously.

Surgical instrument (14) of the present example comprises a handle assembly (18), a shaft assembly (20) extending distally from the handle assembly (18), and an end effector (22) arranged at a distal end of the shaft assembly (20). Handle assembly (18) comprises a body (24) including a pistol grip (26) and energy control buttons (28, 30) configured to be manipulated by a surgeon. A trigger (32) is coupled to a lower portion of body (24) and is pivotable toward and away from pistol grip (26) to selectively actuate end effector (22), as described in greater detail below. In other suitable variations of surgical instrument (14), handle assembly (18) may comprise a scissor grip configuration, for example. As described in greater detail below, an ultrasonic transducer (34) is housed internally within and supported by body (24). In other configurations, ultrasonic transducer (34) may be provided externally of body (24), for example as shown in the exemplary configuration of FIG. 14.

Figure 2:
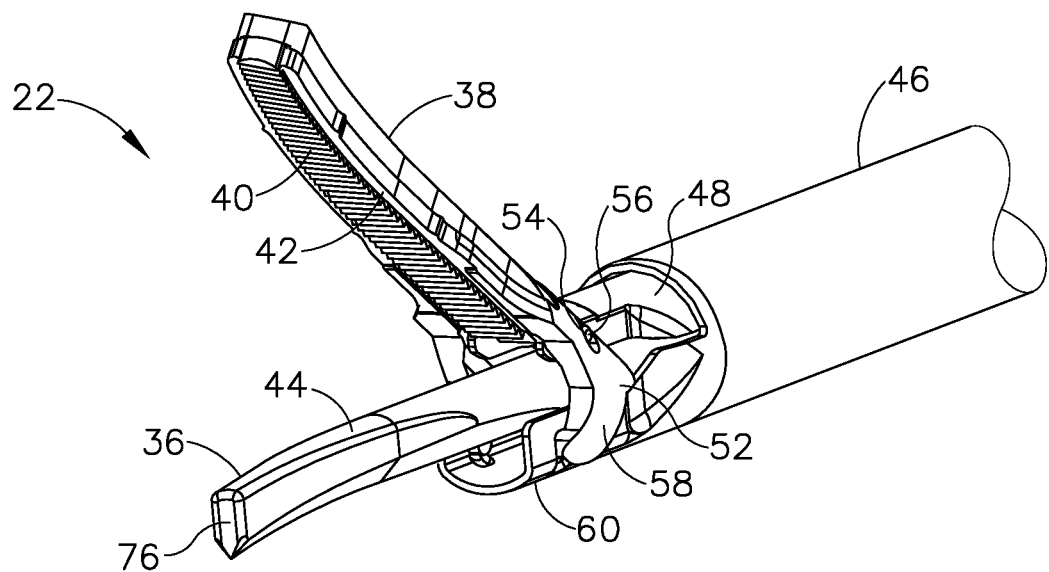
FIG. 2 depicts a top perspective view of an end effector of the surgical instrument of FIG. 1, having a clamp arm that provides a first electrode and an ultrasonic blade that provides a second electrode.
Figure 3:
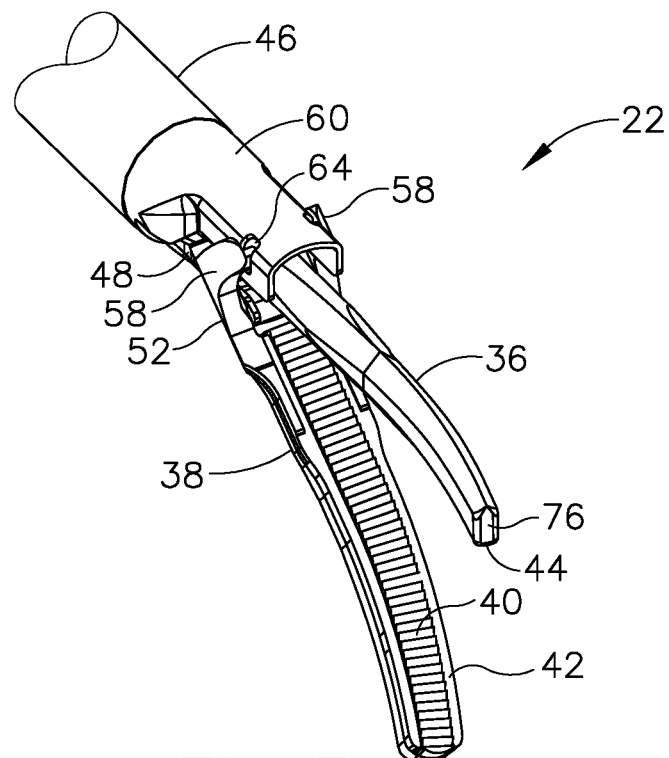
FIG. 3 depicts a bottom perspective view of the end effector of FIG. 2.

As shown in FIGS. 2 and 3, end effector (22) includes an ultrasonic blade (36) and a clamp arm (38) configured to selectively pivot toward and away from ultrasonic blade (36), for clamping tissue therebetween. Ultrasonic blade (36) is acoustically coupled with ultrasonic transducer (34), which is configured to drive (i.e., vibrate) ultrasonic blade (36) at ultrasonic frequencies for cutting and/or sealing tissue positioned in contact with ultrasonic blade (36). Clamp arm (38) is operatively coupled with trigger (32) such that clamp arm (38) is configured to pivot toward ultrasonic blade (36), to a closed position, in response to pivoting of trigger (32) toward pistol grip (26). Further, clamp arm (38) is configured to pivot away from ultrasonic blade (36), to an open position (see e.g., FIGS. 1-3), in response to pivoting of trigger (32) away from pistol grip (26). Various suitable ways in which clamp arm (38) may be coupled with trigger (32) will be apparent to those of ordinary skill in the art in view of the teachings provided herein. In some versions, one or more resilient members may be incorporated to bias clamp arm (38) and/or trigger (32) toward the open position.

A clamp pad (40) is secured to and extends distally along a clamping side of clamp arm (38), facing ultrasonic blade (36). Clamp pad (40) is configured to engage and clamp tissue against a corresponding tissue treatment portion of ultrasonic blade (36) when clamp arm (38) is actuated to its closed position. At least a clamping-side of clamp arm (38) provides a first electrode (42), referred to herein as clamp arm electrode (42). Additionally, at least a clamping-side of ultrasonic blade (36) provides a second electrode (44), referred to herein as a blade electrode (44). As described in greater detail below, electrodes (42, 44) are configured to apply electrosurgical bipolar RF energy, provided by generator (12), to tissue electrically coupled with electrodes (42, 44). Clamp arm electrode (42) may serve as an active electrode while blade electrode (44) serves as a return electrode, or vice-versa. Surgical instrument (14) may be configured to apply the electrosurgical bipolar RF energy through electrodes (42, 44) while vibrating ultrasonic blade (36) at an ultrasonic frequency, before vibrating ultrasonic blade (36) at an ultrasonic frequency, and/or after vibrating ultrasonic blade (36) at an ultrasonic frequency.

As shown in FIGS. 1-5, shaft assembly (20) extends along a longitudinal axis and includes an outer tube (46), an inner tube (48) received within outer tube (46), and an ultrasonic waveguide (50) supported within inner tube (48). As seen best in FIGS. 2-5, clamp arm (38) is coupled to distal ends of inner and outer tubes (46, 48). In particular, clamp arm (38) includes a pair of proximally extending clevis arms (52) that receive therebetween and pivotably couple to a distal end (54) of inner tube (48) with a pivot pin (56) received within through bores formed in clevis arms (52) and distal end (54) of inner tube (48). First and second clevis fingers (58) depend downwardly from clevis arms (52) and pivotably couple to a distal end (60) of outer tube (46). Specifically, each clevis finger (58) includes a protrusion (62) that is rotatably received within a corresponding opening (64) formed in a sidewall of distal end (60) of outer tube (46).

In the present example, inner tube (48) is longitudinally fixed relative to handle assembly (18), and outer tube (46) is configured to translate relative to inner tube (48) and handle assembly (18), along the longitudinal axis of shaft assembly (20). As outer tube (46) translates distally, clamp arm (38) pivots about pivot pin (56) toward its open position. As outer tube (46) translates proximally, clamp arm (38) pivots in an opposite direction toward its closed position. A proximal end of outer tube (46) is operatively coupled with trigger (32), for example via a linkage assembly, such that actuation of trigger (32) causes translation of outer tube (46) relative to inner tube (48), thereby opening or closing clamp arm (38). In other suitable configurations not shown herein, outer tube (46) may be longitudinally fixed and inner tube (48) may be configured to translate for moving clamp arm (38) between its open and closed positions.

Shaft assembly (20) and end effector (22) are configured to rotate together about the longitudinal axis, relative to handle assembly (18). A retaining pin (66), shown in FIG. 4, extends transversely through proximal portions of outer tube (46), inner tube (48), and waveguide (50) to thereby couple these components rotationally relative to one another. In the present example, a rotation knob (68) is provided at a proximal end portion of shaft assembly (20) to facilitate rotation of shaft assembly (20), and end effector (22), relative to handle assembly (18). Rotation knob (68) is secured rotationally to shaft assembly (20) with retaining pin (66), which extends through a proximal collar of rotation knob (68). It will be appreciated that in other suitable configurations, rotation knob (68) may be omitted or substituted with alternative rotational actuation structures.

Figure 5:
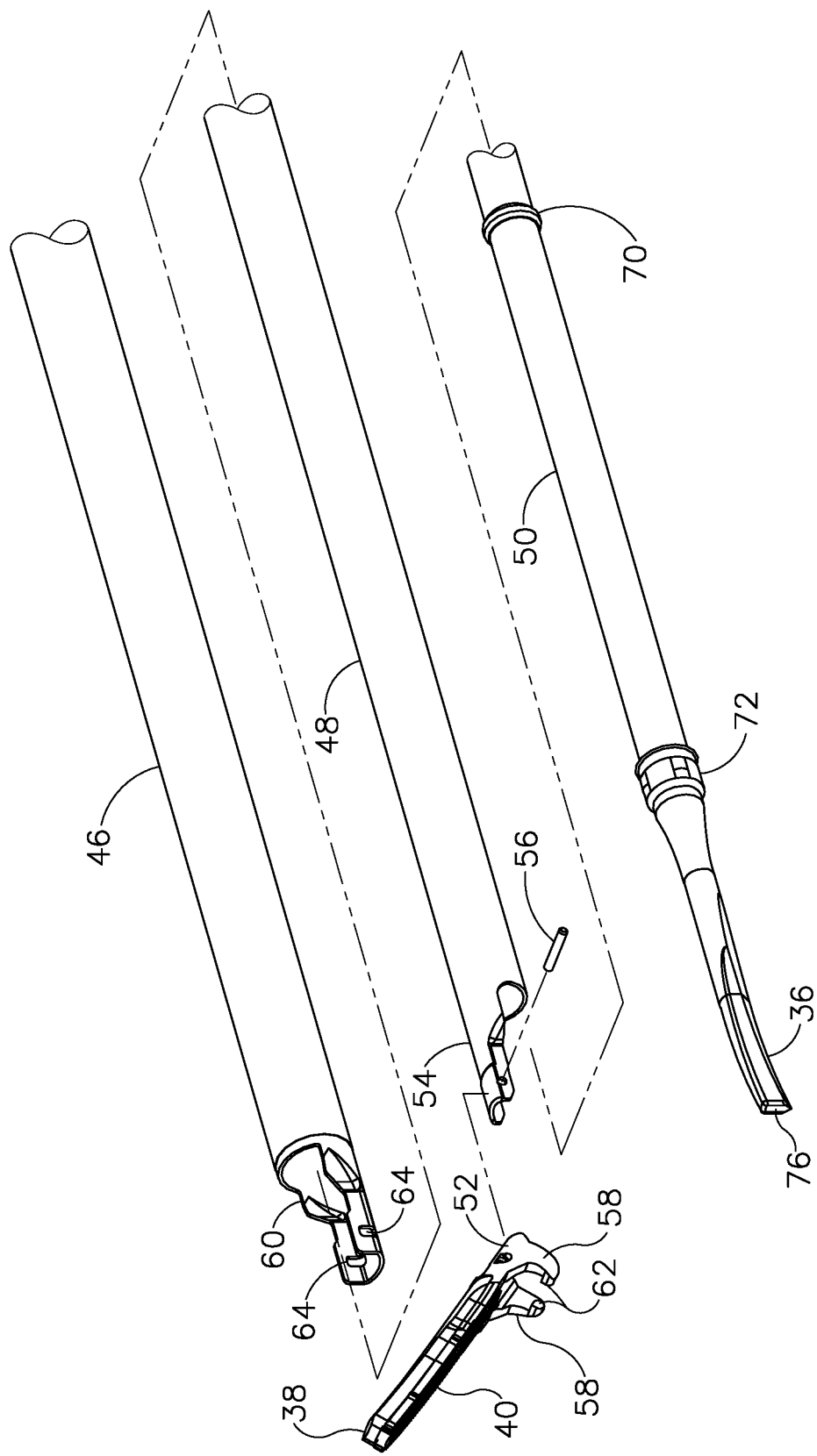
FIG. 5 depicts an enlarged exploded perspective view of a distal portion of the shaft assembly and the end effector of the surgical instrument of FIG. 1.

Ultrasonic waveguide (50) is acoustically coupled at its proximal end with ultrasonic transducer (34), for example by a threaded connection, and at its distal end with ultrasonic blade (36), as shown in FIG. 5. Ultrasonic blade (36) is shown formed integrally with waveguide (50) such that blade (36) extends distally, directly from the distal end of waveguide (50). In this manner, waveguide (50) acoustically couples ultrasonic transducer (34) with ultrasonic blade (36), and functions to communicate ultrasonic mechanical vibrations from transducer (34) to blade (36). Accordingly, ultrasonic transducer (34), waveguide (50), and ultrasonic blade (36) together define acoustic assembly (100). During use, ultrasonic blade (36) may be positioned in direct contact with tissue, with or without assistive clamping force provided by clamp arm (38), to impart ultrasonic vibrational energy to the tissue and thereby cut and/or seal the tissue. For example, blade (36) may cut through tissue clamped between clamp arm (38) and a first treatment side of blade (36), or blade (36) may cut through tissue positioned in contact with an oppositely disposed second treatment side of blade (36), for example during a "back-cutting" movement. In some variations, waveguide (50) may amplify the ultrasonic vibrations delivered to blade (36). Further, waveguide (50) may include various features operable to control the gain of the vibrations, and/or features suitable to tune waveguide (50) to a selected resonant frequency. Additional exemplary features of ultrasonic blade (36) and waveguide (50) are described in greater detail below.

Figure 4:
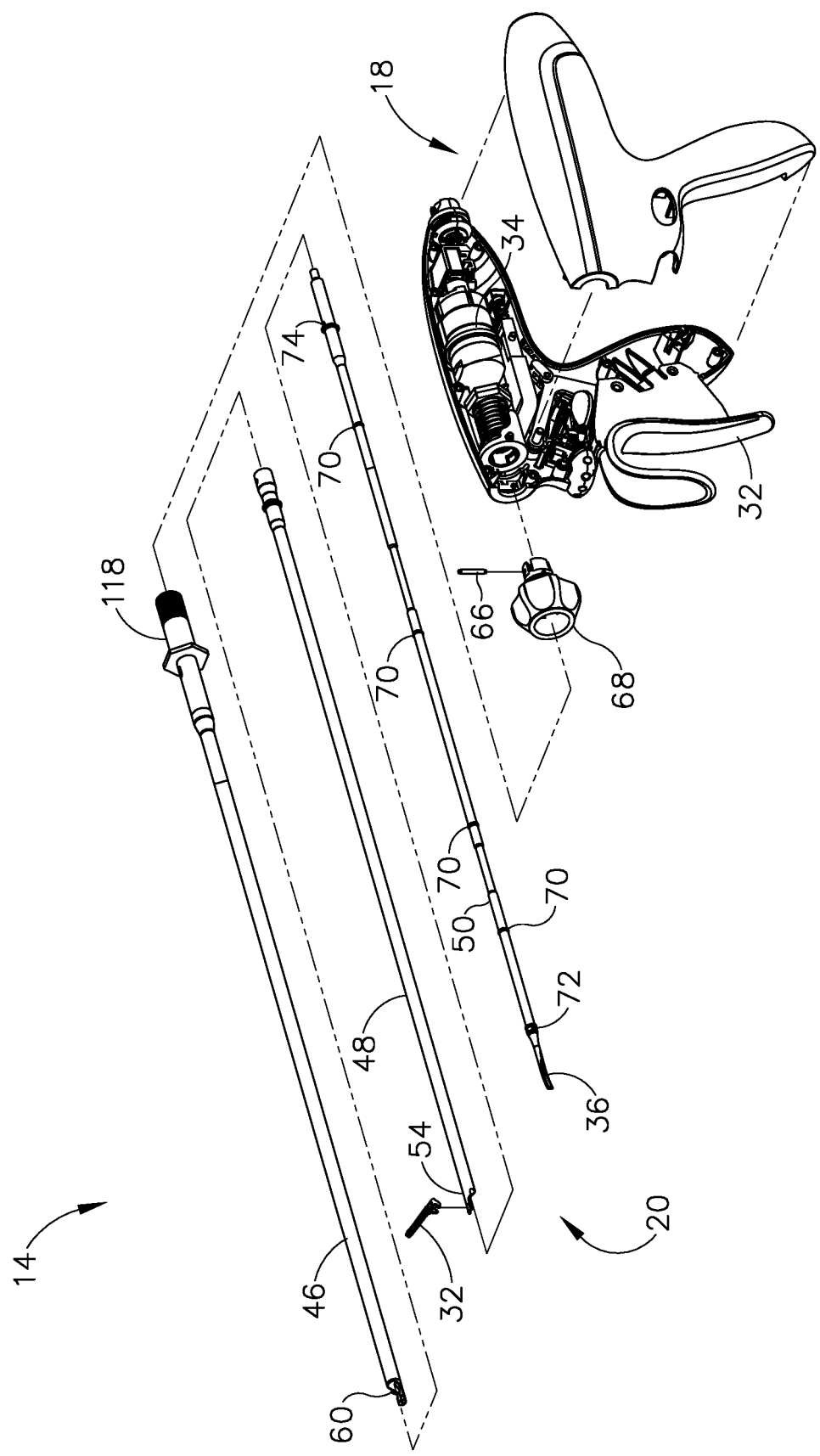
FIG. 4 depicts a partially exploded perspective view of the surgical instrument of FIG. 1.

Waveguide (50) is supported within inner tube (48) by a plurality of nodal support elements (70) positioned along a length of waveguide (50), as shown in FIGS. 4 and 5. Specifically, nodal support elements (70) are positioned longitudinally along waveguide (50) at locations corresponding to acoustic nodes defined by the resonant ultrasonic vibrations communicated through waveguide (50). Nodal support elements (70) may provide structural support to waveguide (50), and acoustic isolation between waveguide (50) and inner and outer tubes (46, 48) of shaft assembly (20). In exemplary variations, nodal support elements (70) may comprise o-rings. Waveguide (50) is supported at its distal-most acoustic node by a nodal support element in the form of an overmold member (72), shown in FIG. 5. Waveguide (50) is secured longitudinally and rotationally within shaft assembly (20) by retaining pin (66), which passes through a transverse through-bore (74) formed at a proximally arranged acoustic node of waveguide (50), such as the proximal-most acoustic node, for example.

In the present example, a distal tip (76) of ultrasonic blade (36) is located at a position corresponding to an anti-node associated with the resonant ultrasonic vibrations communicated through waveguide (50). Such a configuration enables the acoustic assembly (100) of instrument (14) to be tuned to a preferred resonant frequency $f_0$ when ultrasonic blade (36) is not loaded by tissue. When ultrasonic transducer (34) is energized by generator (12) to transmit mechanical vibrations through waveguide (50) to blade (36), distal tip (76) of blade (36) is caused to oscillate longitudinally in the range of approximately 20 to 120 microns peak-to-peak, for example, and in some instances in the range of approximately 20 to 50 microns, at a predetermined vibratory frequency $f_0$ of approximately 50 kHz, for example. When ultrasonic blade (36) is positioned in contact with tissue, the ultrasonic oscillation of blade (36) may simultaneously sever the tissue and denature the proteins in adjacent tissue cells, thereby providing a coagulative effect with minimal thermal spread.

Figure 6:
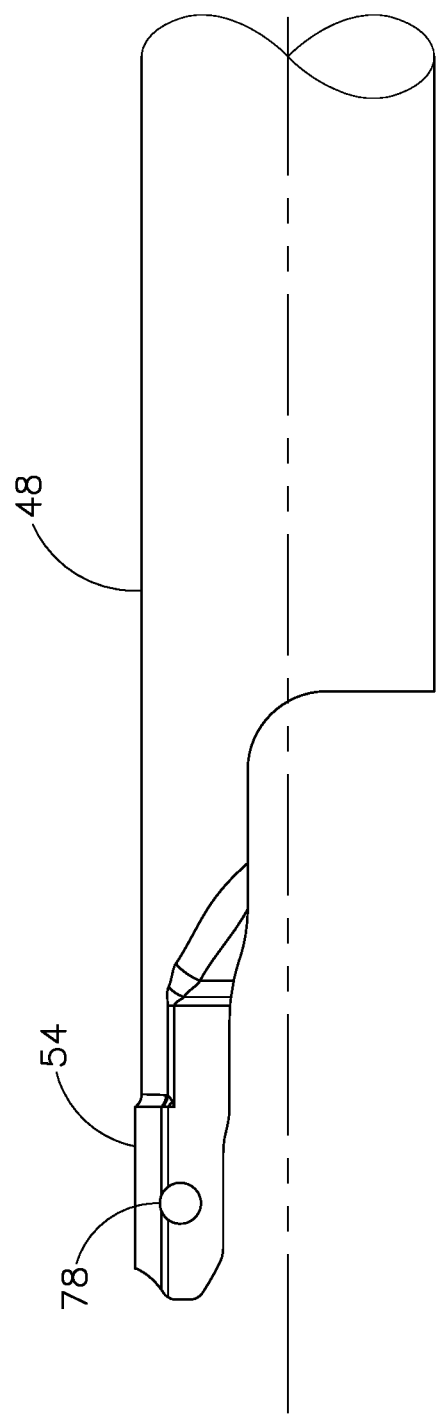
FIG. 6 depicts a side elevational view of a distal portion of an inner tube of the shaft assembly of the surgical instrument of FIG. 1.

As shown in FIG. 6, distal end (54) of inner tube (48) may be offset radially outwardly relative to a remaining proximal portion of inner tube (48). This configuration enables pivot pin bore (78), which receives clamp arm pivot pin (56), to be spaced further away from the longitudinal axis of shaft assembly (20) than if distal end (54) where formed flush with the remaining proximal portion of inner tube (48). Advantageously, this provides increased clearance between proximal portions of clamp arm electrode (42) and blade electrode (44), thereby mitigating risk of undesired "shorting" between electrodes (42, 44) and their corresponding active and return electrical paths, for example during back-cutting when ultrasonic blade (36) flexes toward clamp arm (38) and pivot pin (56) in response to normal force exerted on blade (36) by tissue. In other words, when ultrasonic blade (36) is used in a back-cutting operation, ultrasonic blade (36) may tend to deflect slightly away from the longitudinal axis of shaft assembly (20), toward pin (56). By having pivot pin bore (78) spaced further away from the longitudinal axis than pivot pin bore (78) otherwise would be in the absence of the radial offset provided by distal end

(54) of the present example, distal end (54) provides additional lateral clearance between pivot pin (56) and ultrasonic blade (36), thereby reducing or eliminating the risk of contact between ultrasonic blade (36) and pivot pin (56) when ultrasonic blade (36) deflects laterally during back-cutting operations. In addition to preventing electrical short circuits that would otherwise result from contact between ultrasonic blade (36) and pivot pin (56) when end effector (22) is activated to apply RF electrosurgical energy, the additional clearance prevents mechanical damage that might otherwise result from contact between ultrasonic blade (36) and pivot pin (56) when ultrasonic blade (36) is vibrating ultrasonically.

II. Exemplary Surgical Systems with Power Cables and Cable Adapters

A. Overview of Exemplary Surgical Systems

FIG. 7 shows an exemplary surgical system (400) similar to surgical system (10) in that surgical system (400) includes a generator (402), a surgical instrument (404), and a power cable (406) configured to operatively couple surgical instrument (404) with generator (402). Surgical system (400) further includes a cable adapter (408) configured to couple power cable (406) with an output port on generator (402), which may also function as an input port. Surgical instrument (404) may be in the form of surgical instrument (14), and may incorporate any one or more of the exemplary supplemental or alternative features described above. Surgical instrument (404) includes an internally-mounted ultrasonic transducer (410), which may be in the form of ultrasonic transducer (34), described above.

Power cable (406) includes a first cable end (412) configured to couple with surgical instrument (404), and a second cable end (414) configured to couple with generator (402) via cable adapter (408). In the present example, first cable end (412) is configured to releasably couple to surgical instrument (404), and second cable end (414) is configured to releasably couple to a first adapter end (416) of cable adapter (408). A second adapter end (418) of cable adapter (408) is configured to releasably couple to a port on generator (402). The releasable couplings described above may be achieved using any suitable coupling elements known in the art. By way of example only, such coupling elements may include threaded elements, dynamic snap-fit elements, static snap-fit elements, magnetic elements, and/or friction fit elements. In alternative configurations, any one or more of the releasable couplings described above may be non-releasable. For example, first cable end (412) may be non-releasably attached to surgical instrument (404), and/or second cable end (414) may be non-releasably attached to first adapter end (416). In other configurations, any suitable combination of releasable and non-releasable couplings between surgical instrument (404), power cable (406), cable adapter (408), and generator (402) may be provided.

In the exemplary configuration shown in FIG. 7, first cable end (412) of power cable (406) couples to a proximal end of handle assembly (420) of surgical instrument (404), and aligns coaxially with ultrasonic transducer (410) housed therein. It will be understood, however, that first cable end (412) may couple to handle assembly (420) at various other locations, and/or in various other orientations relative to transducer (410). For example, in one alternative configuration, first cable end (412) may couple to a proximal portion of handle assembly (420) at a location offset from the central axis of ultrasonic transducer (410). In another alternative configuration, first cable end (412) may couple to a lower end of a pistol grip (422) of handle assembly (410).

FIG. 8 shows another exemplary surgical system (500) similar to surgical systems (10, 400) in that surgical system (500) includes a generator (502), a surgical instrument (504), and a power cable (506) configured to operatively couple surgical instrument (504) with generator (502). Surgical system (500) further includes a cable adapter (508) configured to couple power cable (506) with an output port on generator (502). Surgical instrument (504) is similar to surgical instrument (404), except that surgical instrument (504) includes an externally-mounted ultrasonic transducer (510) that releasably couples to and is supported by a handle assembly (520) of surgical instrument (504). Power cable (506) may be substantially similar to power cable (406). Furthermore, generator (502), surgical instrument (504), power cable (506), and cable adapter (508) may be configured to couple to one another in various configurations similar to those described above in connection with surgical system (400).

B. Exemplary Filter Circuitry

Figure 9:
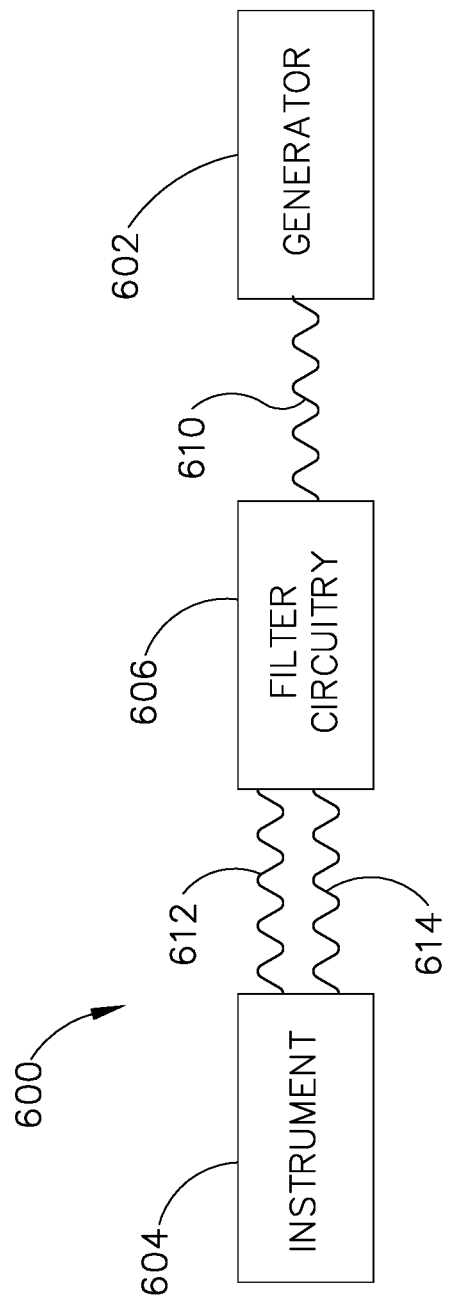
FIG. 9 depicts a schematic view of an exemplary surgical system including a surgical instrument, filter circuitry, and a generator.

FIG. 9 shows another exemplary surgical system (600) including a generator (602), a surgical instrument (604), and filter circuitry (606). Surgical system (600) may represent any of surgical systems (10, 400, 500) described above. In that regard, generator (602) may represent any of generators (12, 402, 502), and surgical instrument (602) may represent any of surgical instruments (14, 404, 504), for example.

Generator (602) is configured to generate and emit a single output waveform (610) (also referred to as a "drive signal") that contains an ultrasonic drive component and an RF drive component. Filter circuitry (606) is configured to receive the single output waveform (610) and separate its ultrasonic and RF drive components. More specifically, filter circuitry (606) converts the single output waveform (610) into an ultrasonic drive waveform (612) and a separate RF drive waveform (614). Ultrasonic drive waveform (612) is configured to drive an ultrasonic transducer of surgical instrument (602) to produce ultrasonic energy for cutting and/or sealing tissue; and an RF drive waveform (614) is configured to energize bipolar RF electrodes of surgical instrument (602) with electrosurgical bipolar RF energy for sealing tissue.

By way of example only, filter circuitry (606) may be constructed and function in accordance with the teachings of U.S. Pub. No. 2017/0086910, entitled "Techniques for Circuit Topologies for Combined Generator," published Mar. 30, 2017, issued as U.S. Pat. No. 10,610,286, on Apr. 7,2020, the disclosure of which is incorporated by reference herein; U.S. Pub. No. 2017/0086908, entitled "Circuit Topologies for Combined Generator," published Mar. 30, 2017, issued as U.S. Pat. No. 11,033,322 on Jun. 15, 2021, the disclosure of which is incorporated by reference herein; U.S. Pub. No. 2017/0086911, entitled "Circuits for Supplying Isolated Direct Current (DC) Voltage to Surgical Instruments," published Mar. 30, 2017, issued as U.S. Pat. No. 10,687,884 on Jun. 23, 2020, the disclosure of which is incorporated by reference herein; U.S. Pub. No. 2017/0086909, entitled "Frequency Agile Generator for a Surgical Instrument," published Mar. 30, 2017, now abandoned, the disclosure of which is incorporated by reference herein; and/or U.S. Pub. No. 2017/0086876, entitled "Method and Apparatus for Selecting Operations of a Surgical Instrument Based on User Intention," published Mar. 30, 2017, the disclosure of which is incorporated by reference herein.

Ultrasonic and RF drive waveforms (612, 614) may be delivered to the ultrasonic transducer and bipolar RF electrodes of surgical instrument (604) simultaneously, such that instrument (604) may treat tissue with simultaneous application of ultrasonic energy and electrosurgical bipolar RF energy. The ultrasonic and RF energies may be applied selectively, and various parameters of the applied energies may be selectively adjusted, using user input features provided on generator (602) and/or on surgical instrument (604), such as energy control buttons (28, 30), for example. In various examples, surgical system (600) may be configured to deliver pre-determined levels and/or patterns of ultrasonic and/or RF energies based on energy application algorithms pre-programmed into control circuitry of surgical system (600). Such algorithms may include any one or more of the exemplary algorithms disclosed in U.S. Pat. No. 8,663,220, entitled "Ultrasonic Surgical Instruments," issued Mar. 4, 2014, incorporated by reference above; U.S. Pub. No. 2017/0000541, entitled "Surgical Instrument with User Adaptable Techniques," published Jan. 5, 2017, incorporated by reference above; and/or any other patents or patent applications incorporated by reference herein.

Figure 10:
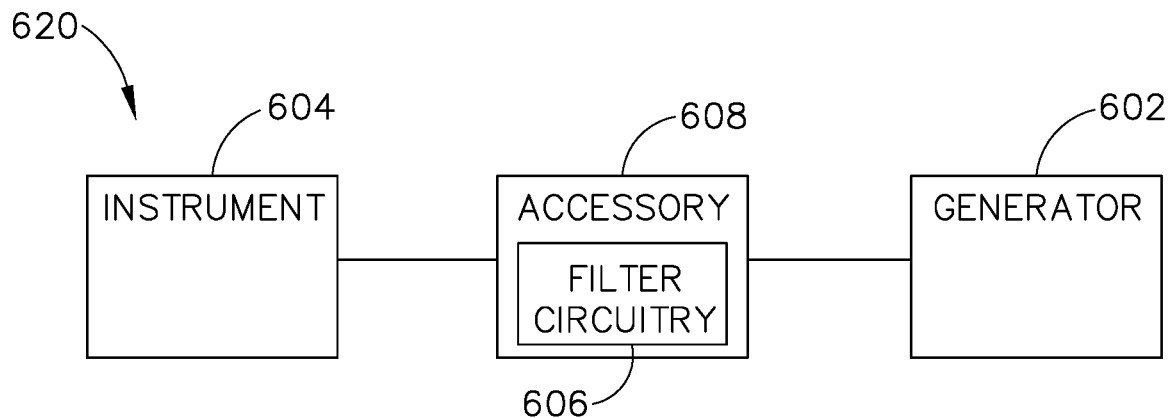
FIG. 10 depicts a schematic view of an exemplary version of the surgical system of FIG. 9, in which the filter circuitry is arranged within an accessory of the surgical system.
Figure 11:
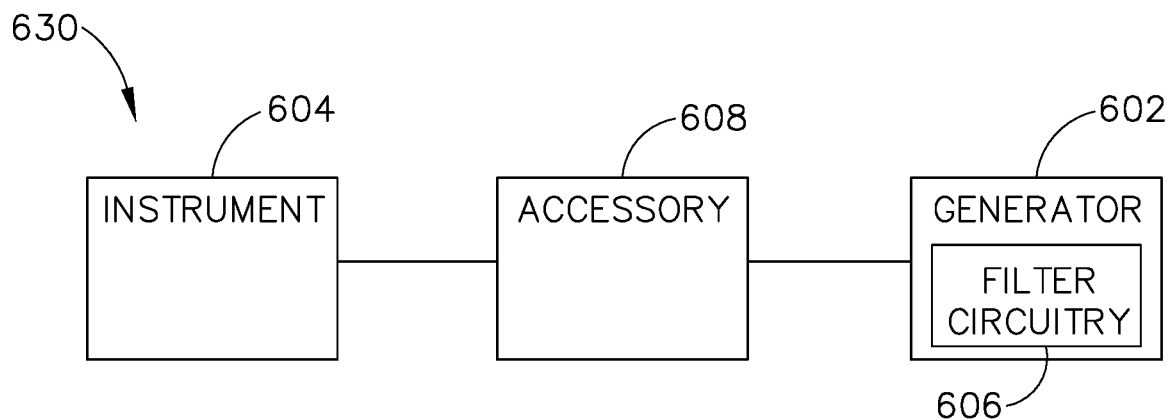
FIG. 11 depicts a schematic view of another exemplary version of the surgical system of FIG. 9, in which the filter circuitry is arranged within the generator of the surgical system.
Figure 12:
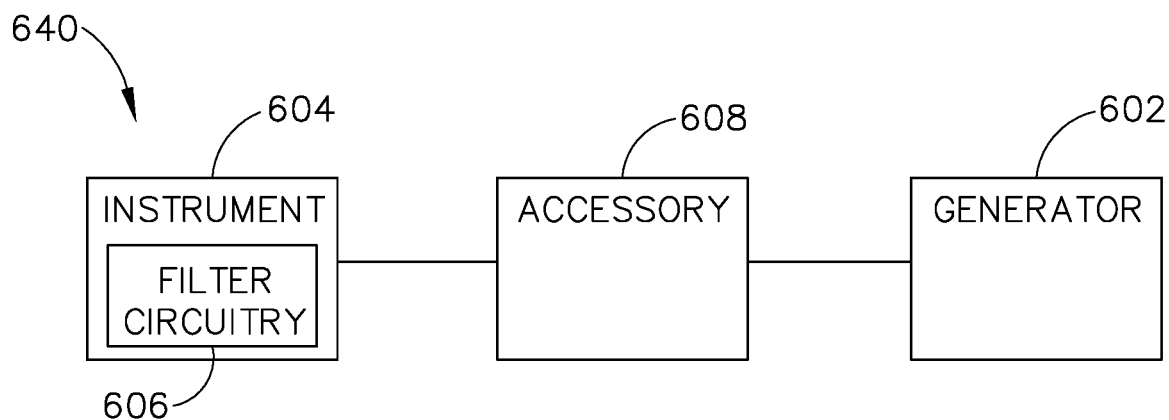
FIG. 12 depicts a schematic view of another exemplary version of the surgical system of FIG. 9, in which the filter circuitry is arranged within the surgical instrument of the surgical system.

Filter circuitry (606) may be arranged at a variety of suitable locations within surgical system (600). FIG. 10 shows a first exemplary version of surgical system (600) in the form of surgical system (620), in which filter circuitry (606) is integrated into an accessory device (608), which may be in the form of a power cable or a cable adapter, such as power cables (406, 506) or cable adapters (408, 508) described above, for example. FIG. 11 shows a second exemplary version of surgical system (600) in the form of surgical system (630), in which filter circuitry (606) is integrated into generator (602). FIG. 12 shows a third exemplary version of surgical system (600) in the form of surgical system (630), in which filter circuitry (606) is integrated into surgical instrument (604).

Figure 13:
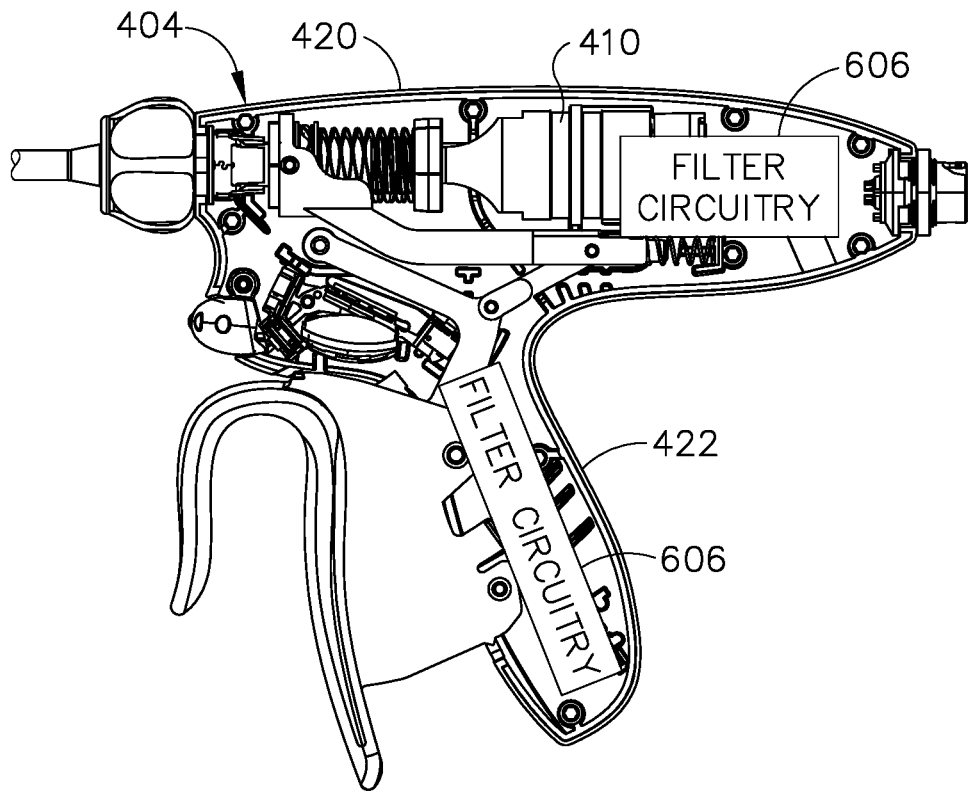
FIG. 13 depicts a side elevational view of the surgical instrument of FIG. 7 with a side body portion of the handle assembly omitted, the surgical instrument including filter circuitry according to the exemplary system configuration of FIG. 12, the filter circuitry schematically shown arranged at several optional locations within the handle assembly.

FIG. 13 shows surgical instrument (404) having filter circuitry (606) arranged therein at various optional locations, in accordance with the general configuration of surgical system (630) of FIG. 12. As shown, and by way of example only, filter circuitry (606) may be arranged within a proximal portion of handle assembly (420), proximally of internally-mounted ultrasonic transducer (410). Alternatively, filter circuitry (606) within a lower portion of pistol grip (422) of handle assembly (420).

Figure 14:
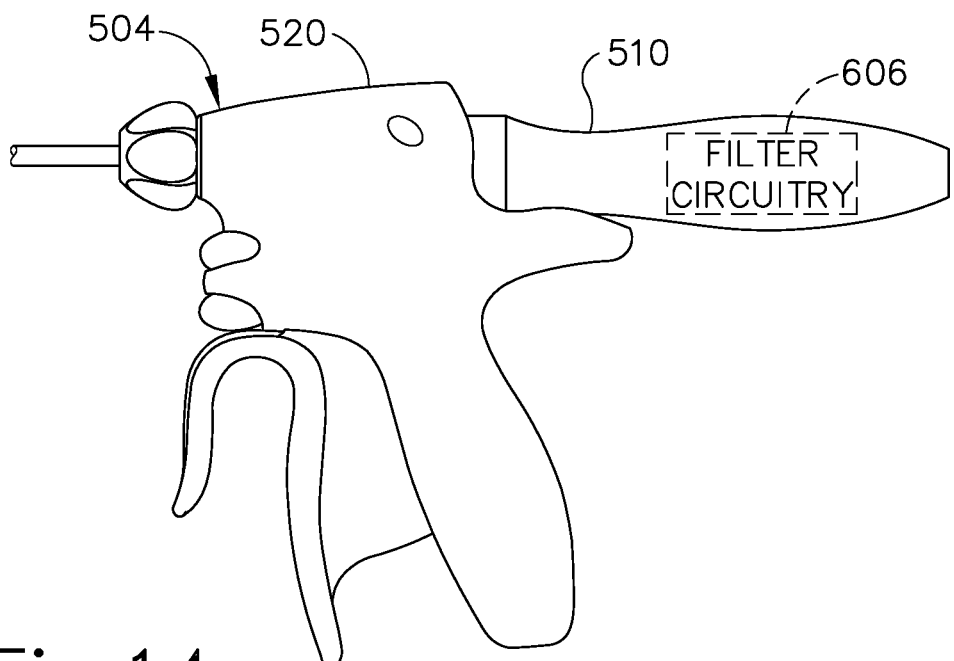
FIG. 14 depicts a side elevational view of the surgical instrument of FIG. 8, the surgical instrument including filter circuitry according to the exemplary system configuration of FIG. 12, the filter circuitry schematically shown arranged within the externally mounted ultrasonic transducer.

FIG. 14 shows surgical instrument (504) having filter circuitry (606) arranged therein, in accordance with the general configuration of surgical system (630) of FIG. 12. As shown, and by way of example only, filter circuitry (606) may be integrated into externally-mounted ultrasonic transducer (510).

C. Exemplary Arrangements of EEPROMs and ASICs

It may be desirable to equip any of the exemplary surgical systems disclosed herein with at least one electrically erasable programmable read-only memory ("EEPROM"), and an application-specific integrated circuit ("ASIC"). For example, one or more EEPROMs may be provided to record and retain certain manufacturing inputs and system settings, and track usage of one or more components of the surgical system, such as the surgical instrument and/or the power cable. Such EEPROMs may be placed in communication with a generator of the surgical system so the generator may read the data collected by the EEPROMs. An ASIC may be provided to receive an analog signal emitted by a component of the surgical instrument, such as energy control buttons (28, 30). In response to receiving the analog signal, the ASIC generates and emits a corresponding digital signal indicating a state of the surgical instrument, the digital signal to be received by the generator. In response to receiving the digital signal, the generator may perform one or more pre-determined actions, such as adjustment of the ultrasonic and/or RF drive components of the output waveform emitted by the generator. It will be understood that each EEPROM and ASIC of the exemplary surgical systems described below may communicate with a generator of the surgical system via a dedicated communication line, which may comprise one or more wires, for example.

FIGS. 15-20 show exemplary surgical systems having a surgical instrument (700) and an accessory device (702), which may be in the form of a power cable or a cable adapter. Each surgical system includes one or more EEPROMs (704) and an ASIC (706). As described below, EEPROMs (704) and ASIC (706) may be arranged in various configurations relative to surgical instrument (700) and accessory device (702). It will be appreciated that any of the exemplary surgical systems described below may represent any of the surgical systems described above. For instance, surgical instrument (700) may represent any of surgical instruments (14, 404, 504, 604), and accessory device (702) may represent any one or more of power cables (406, 506) and cable adapters (408, 508). Further, any of the exemplary surgical systems described below may incorporate a generator similar to any of generators (12, 402, 502, 602) described above.

Figure 15:
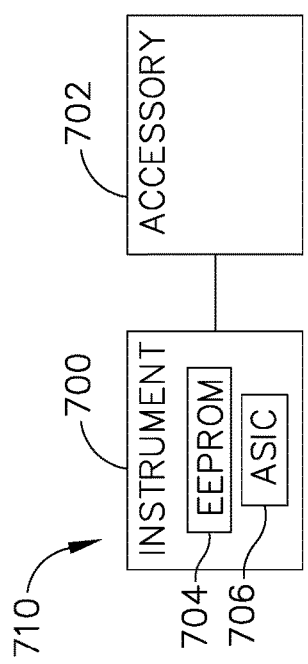
FIG. 15 depicts a schematic view of an exemplary configuration of at least one EEPROM and at least one ASIC arranged relative to a surgical instrument and an accessory operatively associated with the surgical instrument.

FIG. 15 shows a first exemplary surgical system (710) in which an EEPROM (704) and an ASIC (706) are both integrated into surgical instrument (700).

Figure 16:
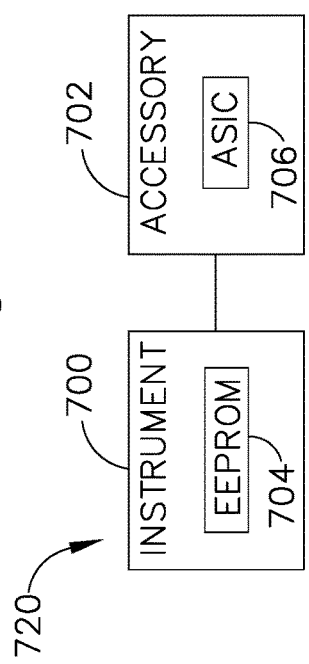
FIG. 16 depicts a schematic view of another exemplary configuration of at least one EEPROM and at least one ASIC arranged relative to a surgical instrument and an accessory operatively associated with the surgical instrument.

FIG. 16 shows a second exemplary surgical system (720) in which an EEPROM (704) is integrated into surgical instrument (700), and an ASIC (706) is integrated into accessory device (702), such as a power cable or a cable adapter of system (720).

Figure 17:
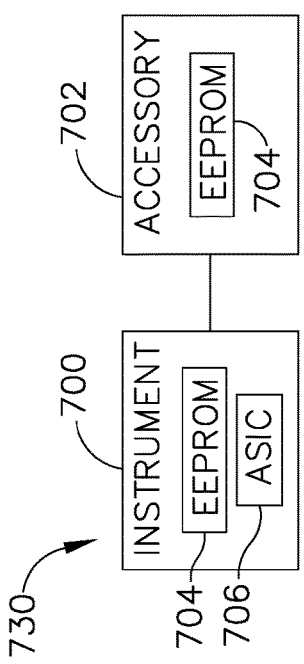
FIG. 17 depicts a schematic view of another exemplary configuration of at least one EEPROM and at least one ASIC arranged relative to a surgical instrument and an accessory operatively associated with the surgical instrument.

FIG. 17 shows a third exemplary surgical system (730) in which a first EEPROM (704) and an ASIC (706) are integrated into surgical instrument (700), and a second EEPROM (704) is integrated into accessory device (702), such as a power cable or a cable adapter of system (730). In such cases, the power cable and cable adapter may be releasably separable or non-separable from one another.

Figure 18:
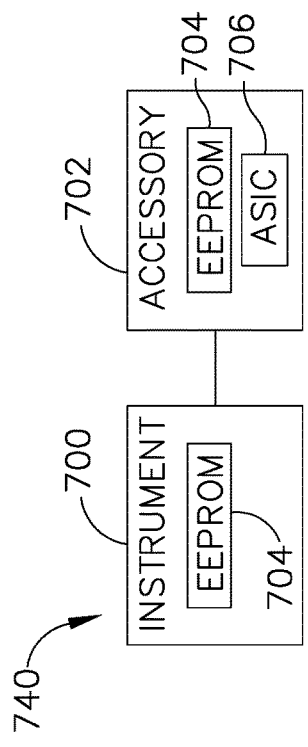
FIG. 18 depicts a schematic view of another exemplary configuration of at least one EEPROM and at least one ASIC arranged relative to a surgical instrument and an accessory operatively associated with the surgical instrument.

FIG. 18 shows a fourth exemplary surgical system (740) in which a first EEPROM (704) is integrated into surgical instrument (700), and a second EEPROM (704) and an ASIC (706) are integrated into accessory device (702). For instance, in one example, second EEPROM (704) and ASIC (706) may both be integrated into a power cable or a cable adapter of system (740). In another example, second EEPROM (704) may be integrated into one of the power cable or the cable adapter, and ASIC (706) may be integrated into the other of the power cable or the cable adapter. In such examples, the power cable and cable adapter may be releasably separable or non-separable from one another.

Figure 19:
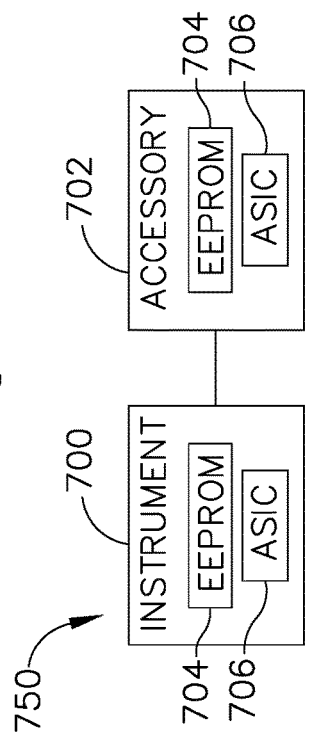
FIG. 19 depicts a schematic view of another exemplary configuration of at least one EEPROM and at least one ASIC arranged relative to a surgical instrument and an accessory operatively associated with the surgical instrument.

FIG. 19 shows a fifth exemplary surgical system (750) in which a first EEPROM (704) and an ASIC (706) are integrated into surgical instrument (700), and second and third EEPROMs (704) are integrated into accessory device (702). For instance, system (750) may include a power cable and a cable adapter that are releasably separable from one another, where the second EEPROM (704) is integrated into the power cable and the third EEPROM (704) is integrated into the cable adapter.

Figure 20:
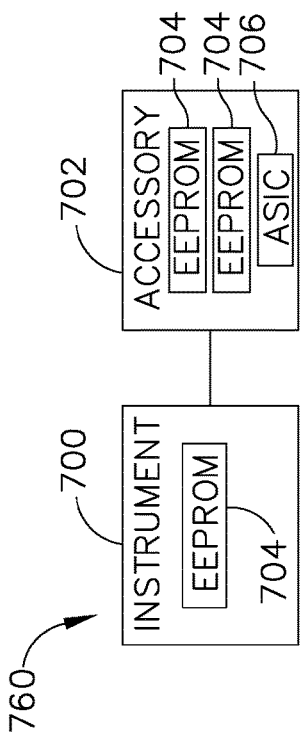
FIG. 20 depicts a schematic view of another exemplary configuration of at least one EEPROM and at least one ASIC arranged relative to a surgical instrument and an accessory operatively associated with the surgical instrument.

FIG. 20 shows a sixth exemplary surgical system (760) in which a first EEPROM (704) is integrated into surgical instrument (700), and second and third EEPROMs (704) and an ASIC (706) are integrated into accessory device (702). For instance, system (760) may include a power cable and a cable adapter that are releasably separable from one another, where the second EEPROM (704) is integrated into the power cable and the third EEPROM (704) and ASIC (706) are integrated into the cable adapter. In another example, the second EEPROM (704) and ASIC (706) may be integrated into the power cable, and the third EEPROM (704) may be integrated into the cable adapter.

Each surgical system (710, 720, 730, 740, 750, 760) described above includes an EEPROM (704) integrated into surgical instrument (700). This instrument EEPROM (704) functions to, among other tasks, track usage of surgical instrument (700), thereby enabling a user to track the number of surgical procedures in which surgical instrument (700) has been used. Surgical systems (730, 740, 750, 760) each include at least one additional EEPROM (704) integrated into a power cable and/or a cable adapter (i.e., an "accessory device") of system (730, 740, 750, 760). Each of these additional accessory EEPROMs (704) tracks usage of the corresponding power cable or cable adapter with which the accessory EEPROM is integrated, thereby enabling a user to monitor usage of the power cable and/or cable adapter separately from usage of surgical instrument (700).

In one or more of exemplary surgical systems (710, 720, 730, 740, 750, 760), accessory device (702) may be releasably coupled with surgical instrument (700) so as to be reusable for multiple surgical procedures, for example with multiple surgical instruments (700). The releasable coupling may be in the form of any of those described above in connection with surgical system (400). Alternatively, accessory device (702) may be non-releasably coupled with surgical instrument (700), so as to be non-reusable and discarded along with used surgical instrument (700) after one or more surgical procedures performed on a single patient, for example. For instance, accessory device (702) may be non-releasably coupled with surgical instrument (700) in surgical systems in which ASIC (706) is integrated into accessory device (702), such as surgical systems (720, 740, 760).

Figure 21:
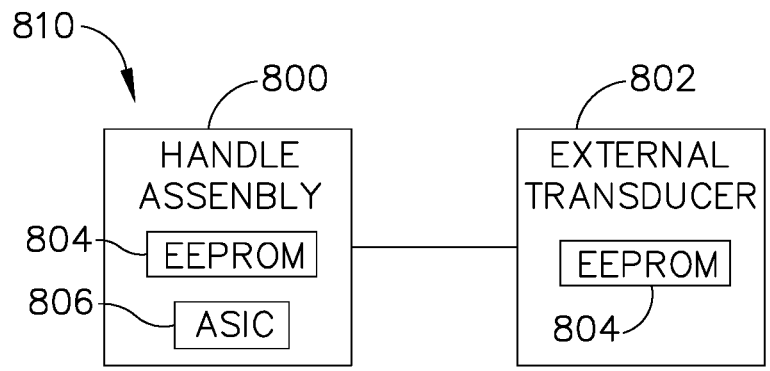
FIG. 21 depicts a schematic view of an exemplary configuration of at least one EEPROM and at least one ASIC arranged within a surgical instrument having a handle assembly and an ultrasonic transducer arranged externally of the handle assembly.
Figure 22:
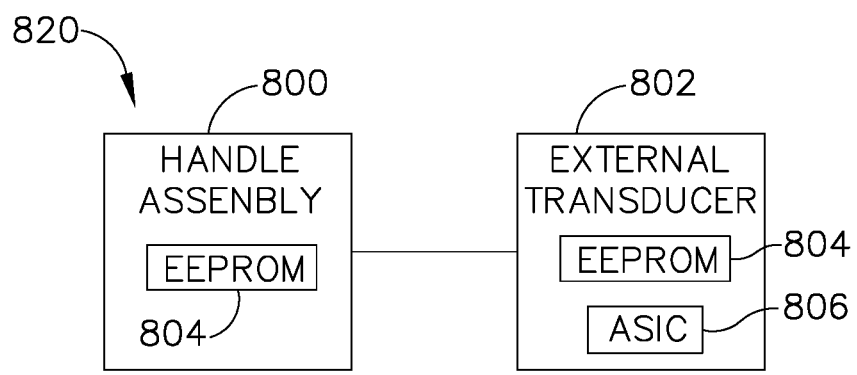
FIG. 22 depicts a schematic view of another exemplary configuration of at least one EEPROM and at least one ASIC arranged within a surgical instrument having a handle assembly and an ultrasonic transducer arranged externally of the handle assembly.
Figure 23:
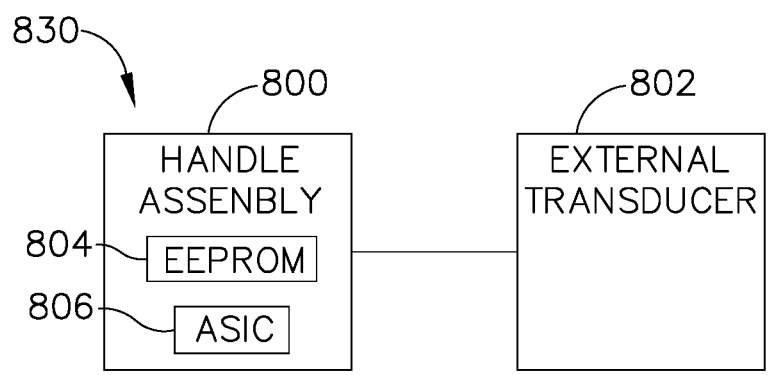
FIG. 23 depicts a schematic view of another exemplary configuration of at least one EEPROM and at least one ASIC arranged within a surgical instrument having a handle assembly and an ultrasonic transducer arranged externally of the handle assembly.

FIGS. 21-23 schematically illustrate exemplary surgical instruments having a handle assembly (800) and an externally-mounted ultrasonic transducer (802) releasably coupled to and supported by handle assembly (800). In that regard, the surgical instruments described below may represent various exemplary configurations of surgical instrument (504) shown in FIGS. 8 and 14. Each surgical instrument includes at least one EEPROM (804) and an ASIC (806), which may be similar in function to EEPROMs (704) and ASICs (706) described above. Some versions of externally-mounted ultrasonic transducer (802) may be configured as reusable components. In addition, or in the alternative, some versions of handle assembly (800) may be configured as reusable components.

FIG. 21 shows a first exemplary surgical instrument (810) in which a first EEPROM (804) and an ASIC (806) are integrated into handle assembly (800), and a second EEPROM (804) is integrated into externally-mounted ultrasonic transducer (802). First EEPROM (804) is configured to track usage of handle assembly (800), while second EEPROM (806) is configured to track usage of external transducer (802) separately from usage of handle assembly (800).

FIG. 22 shows a second exemplary surgical instrument (820) in which a first EEPROM (804) is integrated into handle assembly (800), and a second EEPROM (804) and an ASIC (806) are integrated into externally-mounted ultrasonic transducer (802). First and second EEPROMS (804) are configured to function similarly to those of surgical instrument (810) described above.

FIG. 23 shows a third exemplary surgical instrument (830) having a single EEPROM (804) and an ASIC (806), both of which are integrated into handle assembly (800). In the present example, EEPROM (804) is configured to track usage of handle assembly (800), which may differ from usage of externally-mounted ultrasonic transducer (802), for example if transducer (802) has been used previously in combination with a different handle assembly (800).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical system comprising: (a) a surgical instrument, comprising: (i) a body, (ii) an ultrasonic transducer supported by the body, (iii) a shaft extending distally from the body, and (iv) an end effector arranged at a distal end of the shaft, wherein the end effector is operable to treat tissue with ultrasonic energy; (b) an accessory device configured to operatively couple the surgical instrument with a generator, wherein the generator is operable to power the surgical instrument to provide ultrasonic energy; (c) a primary electrically erasable programmable read-only memory (EEPROM) provided within the body of the surgical instrument, wherein the primary EEPROM is operable to track usage of the surgical instrument; and (d) at least one of: (i) an accessory EEPROM integrated into the accessory device, wherein the accessory EEPROM is operable to track usage of the accessory device, (ii) a transducer EEPROM integrated into the ultrasonic transducer, wherein the transducer EEPROM is operable to track usage of the ultrasonic transducer, or (iii) an accessory application-specific integrated circuit (ASIC) integrated into the accessory device, wherein the accessory ASIC is operable to communicate with the generator regarding a state of the surgical instrument.

Example 2

The surgical system of Example 1, (a) a power cable configured to couple to the surgical instrument; and (b) a cable adapter configured to couple the power cable with the generator, wherein the accessory device comprises one of the power cable or the cable adapter.

Example 3

The surgical system of Example 2, further comprising the accessory EEPROM, wherein the accessory EEPROM is integrated into the power cable.

Example 4

The surgical system of Example 2, further comprising the accessory EEPROM, wherein the accessory EEPROM is integrated into the cable adapter.

Example 5

The surgical system of any of the previous Examples, further comprising an instrument ASIC integrated into the surgical instrument, wherein the instrument ASIC is operable to communicate with the generator regarding a state of the surgical instrument.

Example 6

The surgical system of any of Examples 2 through 5, further comprising the accessory ASIC, wherein the accessory ASIC is integrated into one of the power cable or the cable adapter.

Example 7

The surgical system of Example 6, wherein the accessory ASIC is integrated into the cable adapter.

Example 8

The surgical system of any of the previous Examples, further comprising an instrument ASIC integrated into the surgical instrument, wherein the instrument ASIC is operable to communicate with the generator regarding a state of the surgical instrument.

Example 9

The surgical system of any of Examples 2 through 8, wherein the cable adapter is non-releasably coupled to the power cable.

Example 10

The surgical system of any of Examples 2 through 8, wherein the cable adapter is releasably coupled to the power cable.

Example 11

The surgical system of any of the previous Examples, wherein the ultrasonic transducer is arranged externally of the body.

Example 12

The surgical system of Example 11, further comprising an instrument ASIC provided within one of the body or the ultrasonic transducer.

Example 13

The surgical system of any of the previous Examples, further comprising the transducer EEPROM, wherein the ultrasonic transducer is arranged externally of the body.

Example 14

The surgical system of any of Examples 2 through 13, wherein the surgical system comprises a first EEPROM provided within the body of the surgical instrument, a second EEPROM integrated into the power cable, and a third EEPROM integrated into the cable adapter, wherein the first EEPROM is operable to track usage of the surgical instrument, wherein the second EEPROM is operable to track usage of the power cable independently from usage of the surgical instrument, wherein the third EEPROM is operable to track usage of the cable adapter independently from usage of the surgical instrument and usage of the power cable, wherein the power cable is configured to releasably couple with the surgical instrument and with the cable adapter, wherein the cable adapter is configured to releasably couple with the generator.

Example 15

The surgical system of any of the previous Examples, wherein the end effector comprises: (A) an ultrasonic blade, wherein the ultrasonic transducer is operable to drive the ultrasonic blade with ultrasonic energy, (B) a clamp arm movable relative to the ultrasonic blade for clamping tissue therebetween, (C) a first RF electrode provided by the clamp arm, and (D) a second RF electrode provided by the ultrasonic blade, wherein the first and second RF electrodes are operable to seal tissue with bipolar RF energy provided by the generator.

Example 16

A surgical system comprising: (a) a surgical instrument, comprising: (i) a shaft extending longitudinally, and (ii) an end effector arranged at a distal end of the shaft, wherein the end effector is operable to treat tissue with at least one of ultrasonic energy or RF energy; (b) an accessory device configured to operatively couple the surgical instrument with a generator, wherein the generator is operable to power the surgical instrument to provide at least one of ultrasonic energy or RF energy; (c) a first electrically erasable programmable read-only memory (EEPROM) integrated into the surgical instrument, wherein the first EEPROM is operable to track usage of the surgical instrument; and (d) a second EEPROM integrated into one of the power cable or the cable adapter, wherein the second EEPROM is operable to track usage of the one of the power cable or the cable adapter.

Example 17

The surgical system of Example 16, wherein the second EEPROM is integrated with the cable adapter, wherein the second EEPROM is operable to track usage of the cable adapter.

Example 18

The surgical system of Example 17, wherein the cable adapter is releasably coupled to the power cable, wherein the surgical system further comprises a third EEPROM integrated with the power cable, wherein the third EEPROM is operable to track usage of the power cable.

Example 19

A surgical instrument comprising: (a) a body; (b) an ultrasonic transducer arranged externally of the body; (c) a shaft extending distally from the body; (d) an end effector arranged at a distal end of the shaft, wherein the end effector is operable to treat tissue with ultrasonic energy; (e) an electrically erasable programmable read-only memory (EE-PROM) integrated with the body, wherein the primary EEPROM is operable to track usage of the body; and (f) an application-specific integrated circuit (ASIC) integrated with one of the body or the ultrasonic transducer, wherein the ASIC is operable to communicate with the generator regarding a state of the surgical instrument.

Example 20

The surgical instrument of Example 19, further comprising a second EEPROM integrated with the ultrasonic transducer, wherein the second EEPROM is operable to track usage of the ultrasonic transducer independently from usage of the body.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed May 1, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on May 1, 2018, published as U.S. Pub. No. 2018/0333181 on Nov. 22, 2018; U.S. patent application Ser. No. 15/967,759, entitled "Combination Ultrasonic and Electrosurgical Instrument Having Ultrasonic Waveguide With Distal Overmold Member," filed on May 1, 2018, issued as U.S. Pat. No. 11,051,866 on Jul. 6, 2021; and/or U.S. patent application Ser. No. 15/967,761, entitled "Combination Ultrasonic and Electrosurgical System Having Generator Filter Circuitry," filed on May 1, 2018, published as U.S. Pub. No. 2018/0333184 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on May 1, 2018, published as U.S. Pub. No. 2018/0333182 on Nov. 22, 2018; U.S. patent application Ser. No. 15/697,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018; U.S. patent application Ser. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 2018; U.S. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018; U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018; and/or U.S. patent application Ser. No. 15/967,784, entitled "Combination Ultrasonic and Electrosurgical Instrument and Method for Sealing Tissue in Successive Phases," filed on May 1, 2018, published as U.S. Pub No. 2018/0333190 on Nov. 22, 2018. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical system comprising:
  (a) a surgical instrument, comprising:
    (i) a body,
    (ii) an ultrasonic transducer supported by the body,
    (iii) an acoustic waveguide extending distally from the body, and
    (iv) an end effector arranged at a distal end of the acoustic waveguide, wherein the end effector is operable to treat tissue with ultrasonic energy;
  (b) an accessory device configured to releasably couple to the surgical instrument and a generator, wherein the accessory device is further configured to operatively couple the surgical instrument with the generator operable to power the surgical instrument to provide ultrasonic energy;
  (c) a primary electrically erasable programmable read-only memory (EEPROM) provided within the body of the surgical instrument, wherein the primary EEPROM is configured to track usage of the body; and
  (d) at least one of:
    (i) an accessory EEPROM integrated into the accessory device, wherein the accessory EEPROM is configured to track usage of the accessory device independent of the primary EEPROM configured to track usage of the body for monitoring usage of the body separate from the accessory EEPROM, or
    (ii) a transducer EEPROM integrated into the ultrasonic transducer, wherein the transducer is configured to releasably couple to the acoustic waveguide, and wherein the transducer EEPROM is configured to track usage of the ultrasonic transducer independent of the primary EEPROM configured to track usage of the body for monitoring usage of the body separate from the transducer EEPROM.

2. The surgical system of claim 1, further comprising:
(a) a power cable configured to couple to the surgical instrument; and
(b) a cable adapter configured to couple the power cable with the generator,
wherein the accessory device comprises one of the power cable or the cable adapter.

3. The surgical system of claim 2, further comprising the accessory EEPROM, wherein the accessory EEPROM is integrated into the power cable.

4. The surgical instrument of claim 2, further comprising the accessory EEPROM, wherein the accessory EEPROM is integrated into the cable adapter.

5. The surgical instrument of claim 4, further comprising an instrument application-specific integrated circuit (ASIC) integrated into the surgical instrument, wherein the instrument ASIC is operable to communicate with the generator regarding a state of the surgical instrument.

6. The surgical instrument of claim 4, further comprising an accessory application-specific integrated circuit (ASIC), wherein the accessory ASIC is integrated into one of the power cable or the cable adapter.

7. The surgical system of claim 2, further comprising an accessory application-specific integrated circuit (ASIC), wherein the accessory ASIC is integrated into one of the power cable or the cable adapter.

8. The surgical system of claim 2, further comprising an instrument ASIC integrated into the surgical instrument, wherein the instrument ASIC is operable to communicate with the generator regarding a state of the surgical instrument.

9. The surgical instrument of claim 2, wherein the cable adapter is non-releasably coupled to the power cable.

10. The surgical instrument of claim 2, wherein the cable adapter is releasably coupled to the power cable.

11. The surgical system of claim 1, further comprising the transducer EEPROM, wherein the ultrasonic transducer is arranged externally of the body.

12. The surgical system of claim 1, wherein the end effector comprises:
(A) an ultrasonic blade, wherein the ultrasonic transducer is operable to drive the ultrasonic blade with ultrasonic energy,
(B) a clamp arm movable relative to the ultrasonic blade for clamping tissue therebetween,
(C) a first radiofrequency (RF) electrode provided by the clamp arm, and
(D) a second RF electrode provided by the ultrasonic blade, wherein the first and second RF electrodes are operable to seal tissue with bipolar RF energy provided by the generator.

13. The surgical system of claim 12, wherein at least one of the accessory device or the surgical instrument includes a filter circuitry, wherein the filter circuitry is configured to receive a single output waveform from the generator and convert the single output waveform to an ultrasonic drive component for driving the ultrasonic blade and a RF drive component for driving the at least one of the first or second RF electrodes.

14. The surgical system of claim 1, comprising the accessory EEPROM integrated into the accessory device, wherein the accessory EEPROM is configured to track usage of the accessory device independent of the primary EEPROM configured to track usage of the body for monitoring usage of the body separate from the accessory EEPROM.

15. The surgical system of claim 1, comprising the transducer EEPROM integrated into the ultrasonic transducer, wherein the transducer is configured to releasably couple to the acoustic waveguide, and wherein the transducer EEPROM is configured to track usage of the ultrasonic transducer independent of the primary EEPROM configured to track usage of the body for monitoring usage of the body separate from the transducer EEPROM.

16. A surgical system comprising:
(a) a surgical instrument, comprising:
(i) a shaft extending longitudinally, and
(ii) an end effector arranged at a distal end of the shaft, wherein the end effector is operable to treat tissue with at least one of ultrasonic energy or radiofrequency (RF) energy;
(b) an accessory device configured to operatively couple the surgical instrument with a generator, wherein the generator is operable to power the surgical instrument to provide at least one of ultrasonic energy or RF energy;
(c) a first electrically erasable programmable read-only memory (EEPROM) integrated into the surgical instrument, wherein the first EEPROM is configured to track usage of the surgical instrument;
(d) at least one of a power cable or a cable adapter; and
(e) a second EEPROM integrated into the at least one of the power cable or the cable adapter, wherein the second EEPROM is configured to track usage of the at least one of the power cable or the cable adapter independent of the first EEPROM configured to track usage of the surgical instrument for monitoring usage of the surgical instrument separate from the at least one of the power cable or the cable adapter.

17. The surgical system of claim 16, wherein the second EEPROM is integrated with the cable adapter, wherein the second EEPROM is operable to track usage of the cable adapter.

18. The surgical system of claim 17, wherein the cable adapter is releasably coupled to the power cable, wherein the surgical system further comprises a third EEPROM integrated with the power cable, wherein the third EEPROM is operable to track usage of the power cable.

19. A method of independently monitoring usage of a body of a surgical system and at least one of an accessory device or an ultrasonic transducer of the surgical system, wherein the surgical system has (a) a surgical instrument, comprising: (i) the body, (ii) the ultrasonic transducer supported by the body, (iii) an acoustic waveguide extending distally from the body, and (iv) an end effector arranged at a distal end of the acoustic waveguide, wherein the end effector is operable to treat tissue with ultrasonic energy; (b) an accessory device configured to releasably couple to the surgical instrument and a generator, wherein the accessory device is further configured to operatively couple the surgical instrument with the generator operable to power the surgical instrument to provide ultrasonic energy; (c) a primary electrically erasable programmable read-only memory (EEPROM) provided within the body of the surgical instrument, wherein the primary EEPROM is configured to track usage of the body; and (d) at least one of: (i) an accessory EEPROM integrated into the accessory device, wherein the accessory EEPROM is configured to track usage of the accessory device independent of the primary EEPROM configured to track usage of the body for monitoring usage of the body separate from the accessory EEPROM, or (ii) a transducer EEPROM integrated into the ultrasonic transducer, wherein the transducer is configured to releasably couple to the acoustic waveguide, and wherein the transducer EEPROM is configured to track usage of the ultrasonic transducer independent of the primary EEPROM configured to track usage of the body for monitoring usage of the body separate from the transducer EEPROM, the method comprising:
  (a) monitoring usage of the body via the primary EEPROM as a first usage number; and
  (b) monitoring usage of at least one of the accessory device via the accessory EEPROM or the ultrasonic transducer via the transducer EEPROM as a second usage number independent of the first usage number.

20. The method of claim 19, wherein the first usage number differs from the second usage number.

\* \* \* \* \*